US012633397B2

(12) United States Patent
Tribble et al.

(10) Patent No.: US 12,633,397 B2
(45) Date of Patent: May 19, 2026

(54) METHODS AND SYSTEMS FOR OPTIMIZING DRUG MANAGEMENT

(71) Applicant: CareFusion 303, Inc., San Diego, CA (US)

(72) Inventors: Dennis Anthony Tribble, Ormond Beach, FL (US); Quyen Ly, San Diego, CA (US); Richard Parr, San Diego, CA (US); Maria Consolacion Jaskela, San Rafael, CA (US); Gautam Sampath, San Diego, CA (US); Alan Greubel, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 455 days.

(21) Appl. No.: 17/626,480

(22) PCT Filed: Jul. 14, 2020

(86) PCT No.: PCT/US2020/042017
§ 371 (c)(1),
(2) Date: Jan. 11, 2022

(87) PCT Pub. No.: WO2021/011580
PCT Pub. Date: Jan. 21, 2021

(65) Prior Publication Data
US 2022/0375579 A1 Nov. 24, 2022

Related U.S. Application Data

(60) Provisional application No. 62/874,444, filed on Jul. 15, 2019.

(51) Int. Cl.
*G16H 40/20* (2018.01)
*G16H 20/10* (2018.01)
*G16H 70/40* (2018.01)

(52) U.S. Cl.
CPC ............. *G16H 40/20* (2018.01); *G16H 20/10* (2018.01); *G16H 70/40* (2018.01)

(58) Field of Classification Search
CPC ........ G16H 40/20; G16H 20/10; G16H 70/40; G06Q 10/08
(Continued)

(56) References Cited

U.S. PATENT DOCUMENTS 6,915,265 B1 * 7/2005 Johnson ................. G16H 10/65
705/2
10,990,352 B1 * 4/2021 Artz .................... G06F 16/2228
(Continued)

FOREIGN PATENT DOCUMENTS

CN          108538357 A      9/2018
WO    WO-2014040722 A1      3/2014

OTHER PUBLICATIONS

Zhou, Mapping Partners Master Drug Dictionary to RxNorm using an NLP-based approach, 2012, Journal of Biomedical Informatics , vol. 45, Issue 4, pp. 626-633 (Year: 2012).*
(Continued)

*Primary Examiner* — David J Stoltenberg
*Assistant Examiner* — Tran N Nguyen
(74) *Attorney, Agent, or Firm* — MASCHOFF BRENNAN

(57) ABSTRACT

Systems and methods for optimizing drug management are disclosed. A disclosed system implements a method that includes receiving, from a first client system, a new drug code and drug information associated with new drug code, determining, by the computing system based on the received drug information, a predetermined medication and a first local identifier used by the first client system to identify the predetermined medication, determining, based at least in part on identifying the first local identifier, one or more
(Continued)

second local identifiers that identify the predetermined medication, identifying, based on the one or more second local identifiers, a plurality of second client systems that use the one or more second local identifiers, and automatically providing, an instruction to each of the plurality of second client systems to associate, at the second client system, one or more corresponding second local identifiers with the new drug code.

18 Claims, 6 Drawing Sheets

(58) Field of Classification Search
USPC ......................................................... 705/2–3
See application file for complete search history.

(56) References Cited

U.S. PATENT DOCUMENTS

| | | | | |
|---|---|---|---|---|
| 2007/0164096 | A1 | 7/2007 | Banfield et al. | |
| 2008/0078828 | A1 | 4/2008 | Helmin et al. | |
| 2008/0243548 | A1* | 10/2008 | Cafer ...................... | G16H 40/67 |
| | | | | 705/3 |
| 2012/0209864 | A1* | 8/2012 | Gogolak ................ | G16H 70/40 |
| | | | | 707/E17.058 |
| 2016/0004825 | A1 | 1/2016 | Martin et al. | |
| 2016/0357919 | A1* | 12/2016 | Bojorquez ............. | G16H 70/40 |
| 2017/0076052 | A1* | 3/2017 | Phillips .................. | G16H 70/20 |
| 2018/0301210 | A1* | 10/2018 | Hoff ........................ | G16H 10/60 |
| 2019/0304580 | A1* | 10/2019 | Heath ................... | G06F 40/166 |

OTHER PUBLICATIONS

Saitwal, Cross-terminology mapping challenges: A demonstration using medication terminological systems, 2012 Journal of biomedical informatics. 45. 613-25 (Year: 2012).*

International Search Report and Written Opinion for Application No. PCT/US2020/042017, dated Sep. 16, 2020, 14 pages.

Office Action in Application No. GB2201653.9, dated Jan. 30, 2023, 7 pages.

United Kingdom Office Action for Application No. GB2201653.9, dated Jul. 31, 2023, 8 pages.

United Kingdom Office Action for Application No. GB2201653.9, dated Nov. 30, 2023, 7 pages.

Chinese Office Action for Application No. 202080064656.3, dated Jan. 23, 2025, 7 pages including translation.

Australian Office Action for Application No. 2020315604, dated Mar. 13, 2025, 3 pages.

Chinese Office Action for Application No. 202080064656.3, dated Jul. 19, 2024, 15 pages including translation.

Qian Juncheng et al., "The Coding Rule and Application of Unique Identification Drug Code (YPID) on China Drug Supply Information Platform", Chinese Journal of Health Informatics and Management, vol. 16, Issue 2, pp. 148-151), doi: 10.3969/j.issn. 1672-5166. 2019.02.06, 11 pages including translation.

Xu, Ting et al., "Data Interchange for Hospital Drug Administration System and Network Information Platform", Journal PrevMed Inf Jun1 2008, vol. 24, No. 6, 8 pages including translation.

* cited by examiner

Networked Computer System 108

Processor(s) 202

Communication Interface(s) 204

Memory 206

208

User Interface 210

Display 212

Operating System 226

Communications Module 228

Access Module 230

Drug Management Platform Instance 240

Message Module 232

Local Identifier Module 234

Drug Configuration Module 236

Database Generator Module 238

Parser Module 242

Verification Module 244

Drug Data Management Module 246

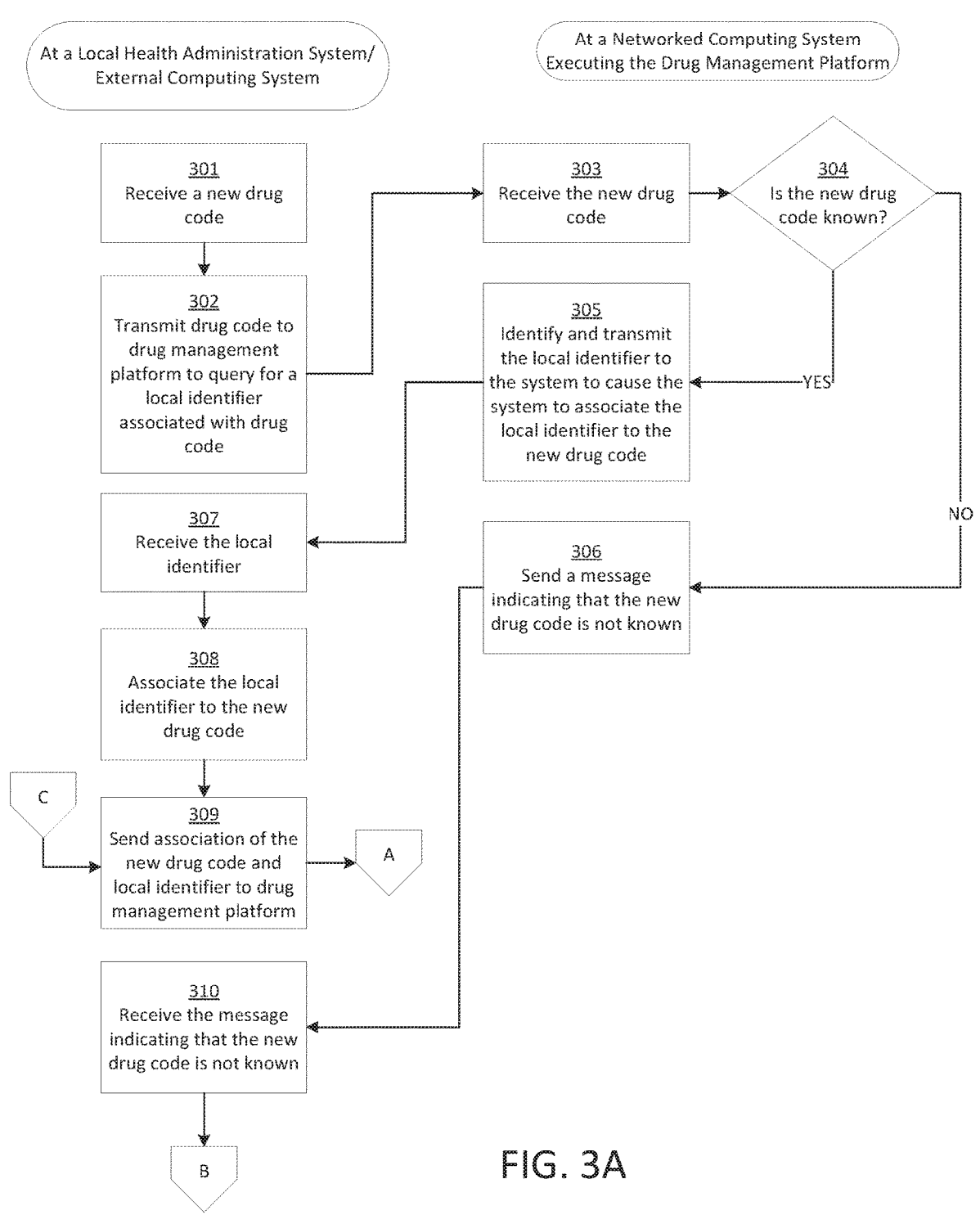

At a Local Health Administration System/
External Computing System

At a Networked Computing System
Executing the Drug Management Platform

301
Receive a new drug
code

302
Transmit drug code to
drug management
platform to query for a
local identifier
associated with drug
code 307
Receive the local
identifier 308
Associate the local
identifier to the new
drug code

C

309
Send association of the
new drug code and
local identifier to drug
management platform

A

310
Receive the message
indicating that the new
drug code is not known

B

303
Receive the new drug
code

304
Is the new drug
code known?

305
Identify and transmit
the local identifier to
the system to cause the
system to associate the
local identifier to the
new drug code

YES

NO

306
Send a message
indicating that the new
drug code is not known

FIG. 3A

METHODS AND SYSTEMS FOR OPTIMIZING DRUG MANAGEMENT

TECHNICAL FIELD

This application relates generally to optimizing drug management within healthcare organizations.

BACKGROUND

As new drug codes are issued more frequently, the number of systems and the number of times a clinician, such as a pharmacist, will have to update data in local drug management systems of a medical facility, such as a hospital, increases. Additionally, a pharmacist may be associated with multiple medical facilities and each medical facility may have a different health administration system that stores information related to the drugs administered by the medical facility in a different form and/or manner within the health administration systems. Thus, for each new drug code, a pharmacist will be burdened by low-value workload of entering the new drug information and associating it with various different existing drug identifiers. Such a process may increase consumption of multiple computing resources of the medical facilities as well as increase the risk of errors during the association of the new drug codes with any existing drug administered by the health facility.

SUMMARY

In one or more implementations, a computer-implemented method of managing drug products includes receiving, by a central computing system from a first client system, a new drug code and drug information associated with new drug code. The method includes determining, by the central computing system based on the received drug information, a predetermined medication and a first local identifier used by the first client system to identify the predetermined medication. The method includes determining, by the central computing system based on identifying the first local identifier, one or more second local identifiers that identify the predetermined medication. The method includes determining, by the central computing system, based on the one or more second local identifiers, a plurality of second client systems that use the one or more second local identifiers. The method includes providing, by the central computing system, an instruction to each of the plurality of second client systems to associate, at the second client system, one or more corresponding second local identifiers with the new drug code. Other aspects include corresponding systems, apparatus, and computer program products for implementation of the method.

In one or more implementations, a system includes a memory storing instructions and one or more processors coupled with the memory and configured to execute the instructions to cause the system to receive, from a first client system, a new drug code and drug information associated with new drug code, determine, based on the received drug information, a predetermined medication and a first local identifier used by the first client system to identify the predetermined medication, determine, based on identifying the first local identifier, one or more second local identifiers that identify the predetermined medication, determine, based on the one or more second local identifiers, a plurality of second client systems that use the one or more second local identifiers, and provide, an instruction to each of the plurality of second client systems to associate, at the second client system, one or more corresponding second local identifiers with the new drug code. Other aspects include corresponding systems, apparatus, and computer program products for implementation of the system.

BRIEF DESCRIPTION OF THE DRAWINGS

For a better understanding of the various described implementations, reference should be made to the Detailed Description below, in conjunction with the following drawings. Like reference numerals refer to corresponding parts throughout the figures and description.

FIGS. 3A-3D show a flow diagram for managing and deploying drug configuration in accordance with some embodiments.

Figure 1:
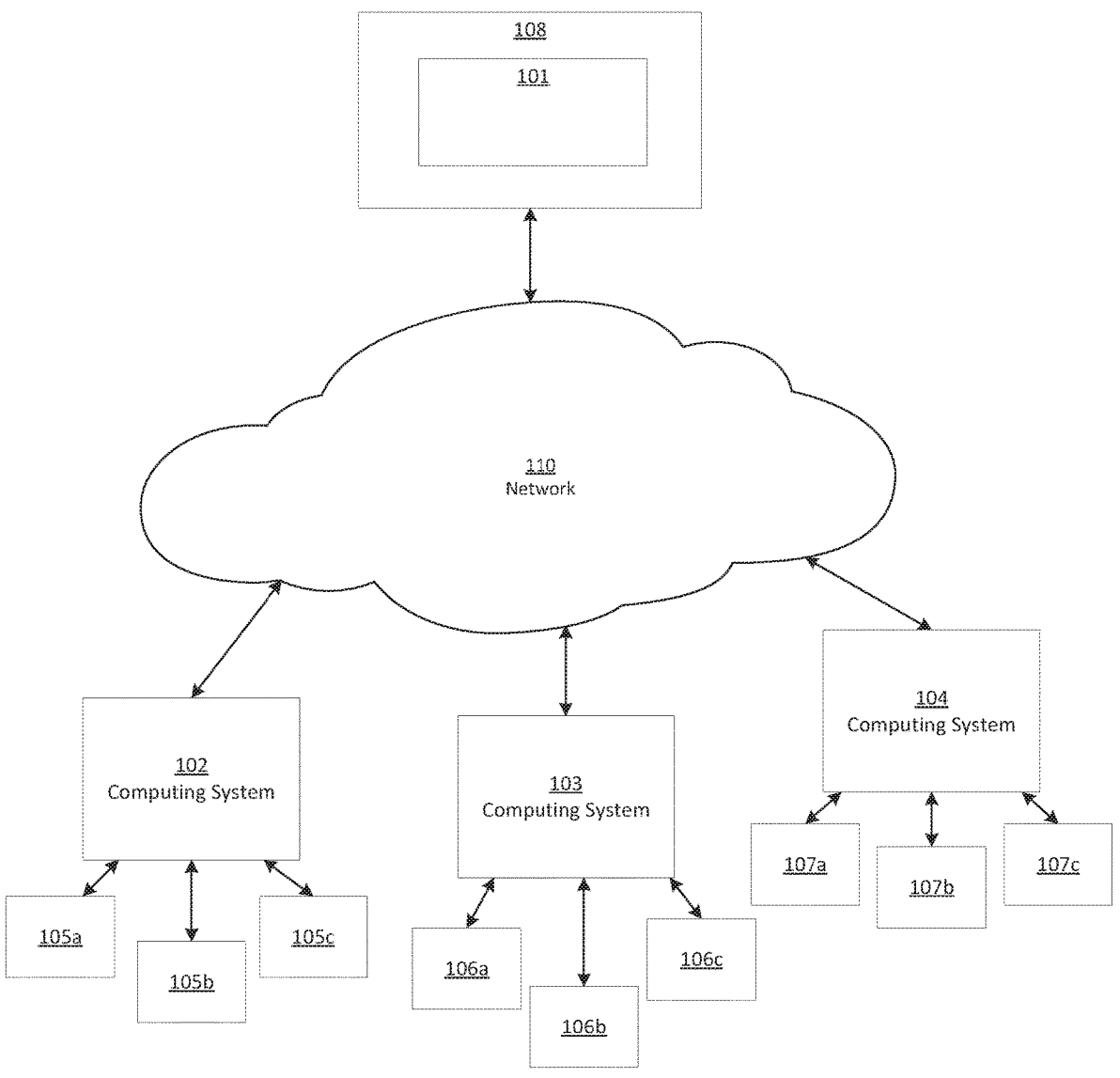
FIG. 1 is a schematic of an example drug management platform in communication with one or more external systems in accordance with some embodiments.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various configurations of the subject disclosure and is not intended to represent the only configurations in which the subject disclosure may be practiced. The appended drawings are incorporated herein and constitute a part of the detailed description. The detailed description includes specific details for the purpose of providing a thorough understanding of the subject disclosure. However, it will be apparent to those skilled in the art that the subject disclosure may be practiced without these specific details. In some instances, structures and components are shown in block diagram form in order to avoid obscuring the concepts of the subject disclosure. Like components are labeled with identical element numbers for ease of understanding.

The terminology used in the description of the various implementations described herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will be further understood that the terms "includes," "including," "comprises," and/or "comprising" when used in the specification, specify the presence of stated features, steps, operations, elements, and/or components, but do not preclude the presence or addition of one or more other features, steps, operations, elements, components, and/or groups thereof.

For the purposes of this disclosure, the term "drug" may refer to a chemical substance that is used therapeutically and which may be used by a generic drug name in one or more official compendia by appropriate authorities (e.g., U.S. Food and Drug Administration (FDA)). In some implementations, a drug may be any substance that, when injected, consumed, inhaled, absorbed on the skin or dissolved under the tongue, causes a physiological (and/or psychological) change in a living body or organism. For the purposes of this disclosure, the term "medication" may refer to a drug at a strength in a dosage form irrespective of a manufacturer and/or packager of the drug. According to various implementations, the term "dispensable" may refer to a medication in any quantity that can be physically provided for patient use irrespective of a manufacturer and/or packager of the dispensable. Likewise, the term "infusible" may refer to a dispensable for intravenous infusion into a patient on an infusion device. Infusibles may include commercially available packages as well as doses compounded pursuant to a prescription or a medication order. In some implementations, the term "product" may refer to a medication as provided by a specific vendor in a specific formulation. In some implementations, a product may be specified by a portion of an identifier of a drug specified by a regulatory authority, such as the FDA. For example, a product may be specified by first two segments of a U.S. National Drug Code—NDC. In some implementations, the term "package" may refer to medication at a specific manufacturer and/or repackager at a specific quantity. A package may be specified by a regulatory identifier, such as the NDC.

According to various implementations, the term "drug code" refers to an identifier that may be used to identify a manufactured drug product (including, e.g., a medication). A drug code may include one or more identifiers assigned by a regulatory authority and/or by a manufacturer and/or packager of a manufactured drug product. Examples of a drug code include, but are not limited to, a U.S. National Drug Code. Likewise, the term "drug information" or information related to drug code may include, but is not limited to, drug name (e.g., ingredient), dosage form, strength or amount of drug, quantity, presences and/or absence of preservatives, presence and/or absences of alcohol, one or more therapeutic classes of the drug, and/or list of regulatory identifiers (e.g., NDCs) that represent manufacturer-specific instances of the drug represented by the drug code. In some implementations, the information related to a labeler (e.g., manufacturer, repackager, distributer, and the like), information related to a specific strength, dosage form (i.e., capsule, tablet, liquid, and the like), a formulation of the drug, information related to a type (e.g., capsule, tablet, liquid, and the like), package size (e.g., 100 capsules) of the drug, chemicals of a drug or mixture of chemicals along with therapeutic properties of the drug, dosage information of the drug in the form of strength of a particular dosage, consumable form information (e.g., tablet, capsule, extended-release tablet, extended-release capsule, injectable solution, powder for injection, injectable suspension, injectable emulsion, and the like) of the drug, manufacturer information of the drug, specific package information along with a specific quantity, regulatory identifier, and/or the like. The term "predetermined medication" (or drug) encompasses any known drug or medication, including but not limited to any drug identifiable by any of the foregoing drug information.

The present disclosure is directed to systems and methods of optimizing management of drugs across various systems of a healthcare organization. In particular, the present disclosure is directed to the use of a global drug management platform for identifying a new drug code within a supply chain of drugs, and updating and/or managing the process of updating various systems of various healthcare organization with the new drug code information. For example, a healthcare organization, such as a hospital, a healthcare service provider, an integrated delivery network, and the like, may identify that a particular drug is currently not associated with a drug code within the administration systems of a medical facility of the healthcare organization. The medical facility may have multiple administration systems, and a healthcare organization may have several medical facilities, resulting in a large number of administration systems (often spanning multiple geographic locations) that may have to be updated with the new drug code. Clinicians, such as pharmacists, associated with the healthcare organization may seek to update one or more of the different administration systems with the new drug code. Due to the large number of administration systems and the different administration systems within a single healthcare organization, updating even a subset of the administration systems may consume a large amount of time, resources, and significantly increase the risk of human error while updating the different administration systems.

The present disclosure provides a drug management platform which provides various healthcare organizations (as customers or clients) with a centralized mechanism for maintaining drug information, including drug codes, consistent across all of the healthcare organizations, irrespective of any localized practice that may differ between organizations. According to various implementations, the drug management platform described herein may be configured to receive new drug code information from a healthcare organization, and, based on certain drug information associated with the new drug code, the drug management platform may be configured to determine certain predetermined medication information stored within a data storage unit of the drug management platform. The drug management platform described herein may be configured to identify the different administration systems of the different healthcare organizations that may have to be updated with the new drug code, and provide instructions to the different administration systems to update their respective systems with the new drug code data. In some implementations, the drug management platform described herein automatically updates the administration systems with the new drug code data. Accordingly, the drug management platform described herein may be configured to crowdsource drug information or updates to a drug, or identification of a new drug, from different healthcare organizations and update the crowd sourced drug data to different other healthcare organizations.

The drug management platform described herein reduces the time required to update various administration systems of a healthcare organization with new drug code data, while reducing the risk of errors while performing such an update.

Turning now to FIG. 1, an example arrangement of a drug management platform in communication with one or more external systems for managing and deploying drug configuration data is shown. FIG. 1 depicts a networked computer system 108 that includes a drug management platform 101 communicatively coupled to one or more external computing systems 102, 103, 104, via a network 110. In some implementations, the drug management platform 101 may include one or more modules and/or sub-platforms that form an enterprise master sub-platform and may be configured to determine, identify, and/or select enterprise level information of one or more enterprises for various drug codes. The drug management platform 101 may include one or more modules and/or sub-platforms that form a global master sub-platform and may be configured to determine, identify, and/or select global information associated with various drug codes. Additional information related to the drug management platform 101, the enterprise sub-platform, and/ or the global master sub-platform are described herein with reference to FIGS. 2 and 3.

The external nature of the computing systems 102, 103, or 104 arises from a separation from the drug management platform. For example, the computing systems may be located across several different sites of a healthcare delivery network. Each system may be communicatively coupled to a centrally located drug management platform of a third-party service provider such as a health information system provider, in some implementations, network 108 may be a public communication network, such as the Internet, cellular telephone networks, mobile data networks, wide area networks, local area networks, metropolitan area networks, and the like. In some implementations, network 108 may be a private communication network, such as a private local area network, leased lines, and the like. In some implementations, the network 108 may be combination of public and private communication networks.

The external computing systems 102, 103, 104, may be associated with, owned, and/or controlled by different clients (e.g., customers) of the drug management platform 101. Examples of such clients may include, but are not limited to, hospitals, integrated delivery networks, health care service providers, and the like. In some implementations, the external computing systems 102, 103, 104 may be designated as core and/or main computing systems of the corresponding customers or clients, and may be granted communication privileges by the drug management platform 101 such that the external computing systems 102, 103, 104 may transfer data to and/or receive data from the drug management platform 101.

The external computing systems 102, 103, 104, may be communicatively coupled to various local healthcare administration systems, such as patient administration systems, healthcare service provider facility administration systems, and/or local drug administration systems, of various medical and/or healthcare service provider facilities. For example, computing system 102 may be communicatively coupled to local health administration systems 105a, 1105b, 105c, collectively referred to herein as local health administration systems 105, and computing system 103 may be communicatively coupled to local health administration systems 106a, 1106b, 106c, collectively referred to herein as local health administration systems 106, and computing system 104 may be communicatively coupled to local health administration systems 107a, 107b, 107c, collectively referred to herein as local health administration systems 107. In some implementations, the local health administration systems 105, 106, 107 may be patient information systems, medical facility administration systems, and/or local instances of a medication management systems.

The local health administration systems 105, 106, 107 may be configured to execute or run patient, healthcare service provider facility, and/or drug administration systems from different vendors. The local health administration systems 105, 106, 107 and/or the systems executing or running therein, may store information related to the drugs administered at facilities of the clients in different manners and/or forms. These differences may include the association between a drug and any corresponding information using different identifiers, referred to herein as "local identifiers." For example, the local health administration system 105a may be configured to execute an electronic medical record (EMR) system of a first vendor and may associate stored data related to the drug Vicodin HP 10 mg capsule with a local identifier "BxR10c," the local health administration system 105b may be configured to execute an EMR of a second vendor and may associate stored data related to the drug Vicodin HP 10 mg capsule with a local identifier "ZXYc10," and the local health administration system 105c may be configured to execute an EMR of a third vendor and may associate stored data related to the drug Vicodin HP 10 mg capsule with a local identifier "JrS10 mgC." Thus, a single drug administered at facilities of a client may be associated with multiple local identifiers.

A user, such as a pharmacy technician and/or a pharmacist, may enter a new drug code into the local health administration systems 105, 106, 107, and the health administration systems 105, 106, 107, may be configured to generate new local identifiers for the new drug code, and, in some implementations, the local health administration systems 105, 106, 107 may be configured to transfer the new local identifiers, the new drug code, and data related to the drug. The computing systems 102, 103, 104, may be configured to receive and/or store local identifiers of a drug and related data from local health administration systems, such as local health administration systems 105, 106, 107, that are communicatively coupled to the computing systems 102, 103, 104. The computing systems 102, 103, 104 may be configured to receive a new drug code information from one or more of the local health administration systems. The computing systems 102, 103, 104, may be configured to transfer new drug code information to the drug management platform 101. For example, if computing system 102 receives new drug code information from a local health administration system, the computing system 102 may transmit the new drug code information to the drug management platform 101 to ensure accuracy and consistency of the drug code information across devices, such as those shown in FIG. 1. In some implementations, the computing systems 102, 103, 104, may be configured to transfer the drug code information in one or more encrypted messages. In some implementations, new drug code information may be associated with the one or more local identifiers of the drug within computing systems 102, 103, 104, including any local health administration systems communicatively coupled to the computing systems 102, 103, 104, such as local health administration systems 105, 106, 107.

The drug management platform 101 may be configured to store, update, validate, and/or maintain data related to local identifiers, drug codes associated with the local identifiers, drug information of drugs, drug codes and/or the local identifiers, predetermined medication data of drugs in one or more data storage units (not shown separately) communicatively coupled to the networked computing system 108. In some implementations, for each drug, and/or drug code, the drug management platform 101 may be configured to associate corresponding data related to local identifiers, drug codes associated with the local identifiers, drug information of drugs, drug codes and/or the local identifiers, predetermined medication data of the drug, and the like with a unique drug management platform 101 identifier, referred to herein as "global platform identifier." Such stored and associated data may be referred to herein as "drug data of the drug management platform 101."

The drug management platform 101 may be configured to receive messages from the computing systems 101, 102, 103. The drug management platform 101 may be configured to determine whether the received messages indicate a new drug code identified at a respective medical facility. In some implementations, upon determining that received message indicates that a new drug code has been identified, the drug management platform 101 verifies that a local identifier of a drug at the medical facility is appropriately associated with the new drug code, determines other local identifiers of the drug within other computing systems of the medical facility and the other computing systems of other facilities, generates databases that associate the local identifiers with the new drug code, transfers messages to the medical facility indicating the associations of the new drug code with local identifiers, and/or automatically update drug management systems of the medical facilities with the association between the local identifiers of the medical facility and the new drug code. Thus, the drug management platform 101 crowd sources new drug codes and optimizes the process of updating drug management and/or administration systems at different medical facilities of facilities, such as hospitals, healthcare service providers, independent delivery networks, and the like. In some implementations, information of a drug code (e.g., drug concept, medication concept, dispensable concept, and the like) may be stored in association with the drug code in a third party data storage system, such as a data storage system associated with a regulatory body (e.g., FDC), and the drug management platform 101 may be configured to validate information of a drug code by comparing information stored in association in the third party data storage system matches the information in a computing system of an enterprise. For example, if information stored in association with a drug code in a data storage system associated with a regulatory body describes an Acetaminophen (TYLENOL) 325 mg tablet, then the drug management platform 101 determines whether the information stored in association with a local identifier of a computing system of an enterprise to which the drug code is associated, also describes an Acetaminophen 325 mg tablet, in some implementations, one or more of the drug concept, medication concept, dispensable concept, infusible concept, product concept, package concept of the drug code may be codified using numbers, alphabets, other characters, and/or a combination thereof, and the drug management platform 101 may be configured to verify such information of the drug code by comparing the corresponding codes. In some implementations, the drug management platform 101 may be configured to validate a drug code by determining whether the drug code was previously associated with a different drug concept, medication concept, and the like in a data storage system associated with the drug management platform 101. In some implementations, the drug management platform 101 may be configured to determine whether the drug code as received exists in a data storage system associated with a regulatory body. In some implementations, the drug management platform 101 may be configured to perform various checksum operations to determine whether the drug code as received matches the drug code as sent by a computing system of an enterprise.

The drug management platform 101 may be an application or an instance of an application hosted on a networked computer system 110. In some implementations, the networked computer system 110 may be an application server computer that is configured to host one or more applications and/or one or more instances of an application, such as one or more instances of the drug management platform 101. Additional details of the networked computer system and the drug management platform 101 are described herein and with reference to FIGS. 2 and 3.

Figure 2:
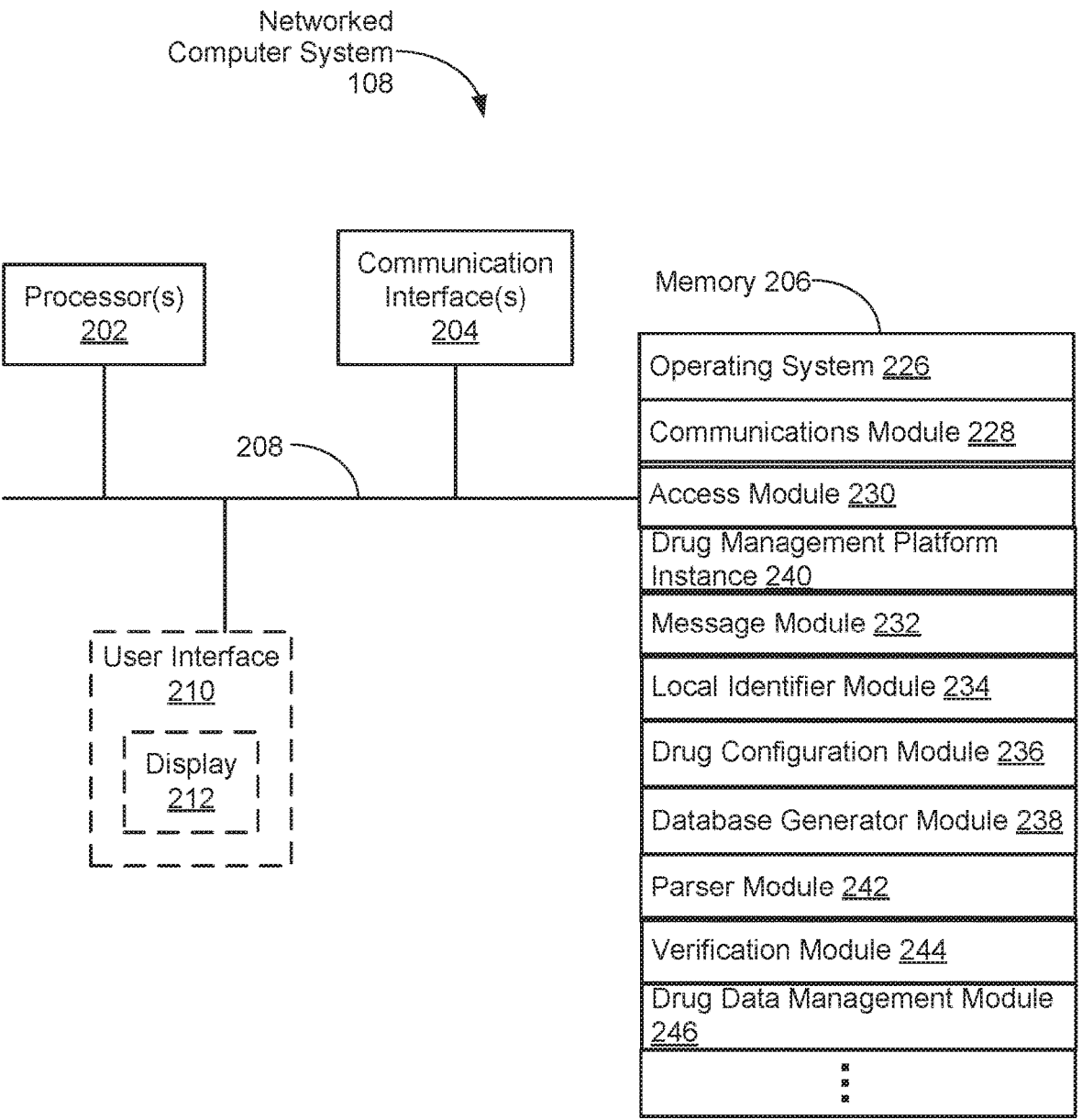
FIG. 2 is a block diagram of an exemplary server system in accordance with some embodiments.
Figure 3B:
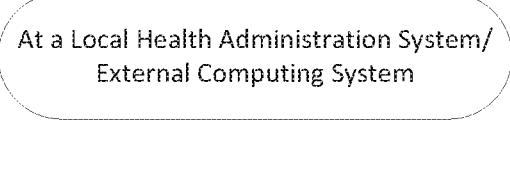
Figure 3B:
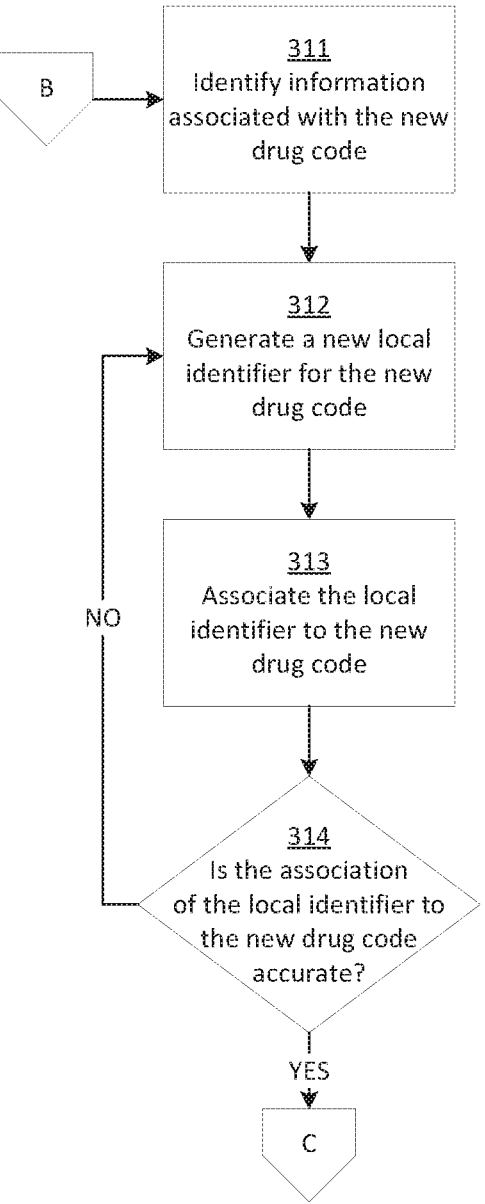
Figure 3C:
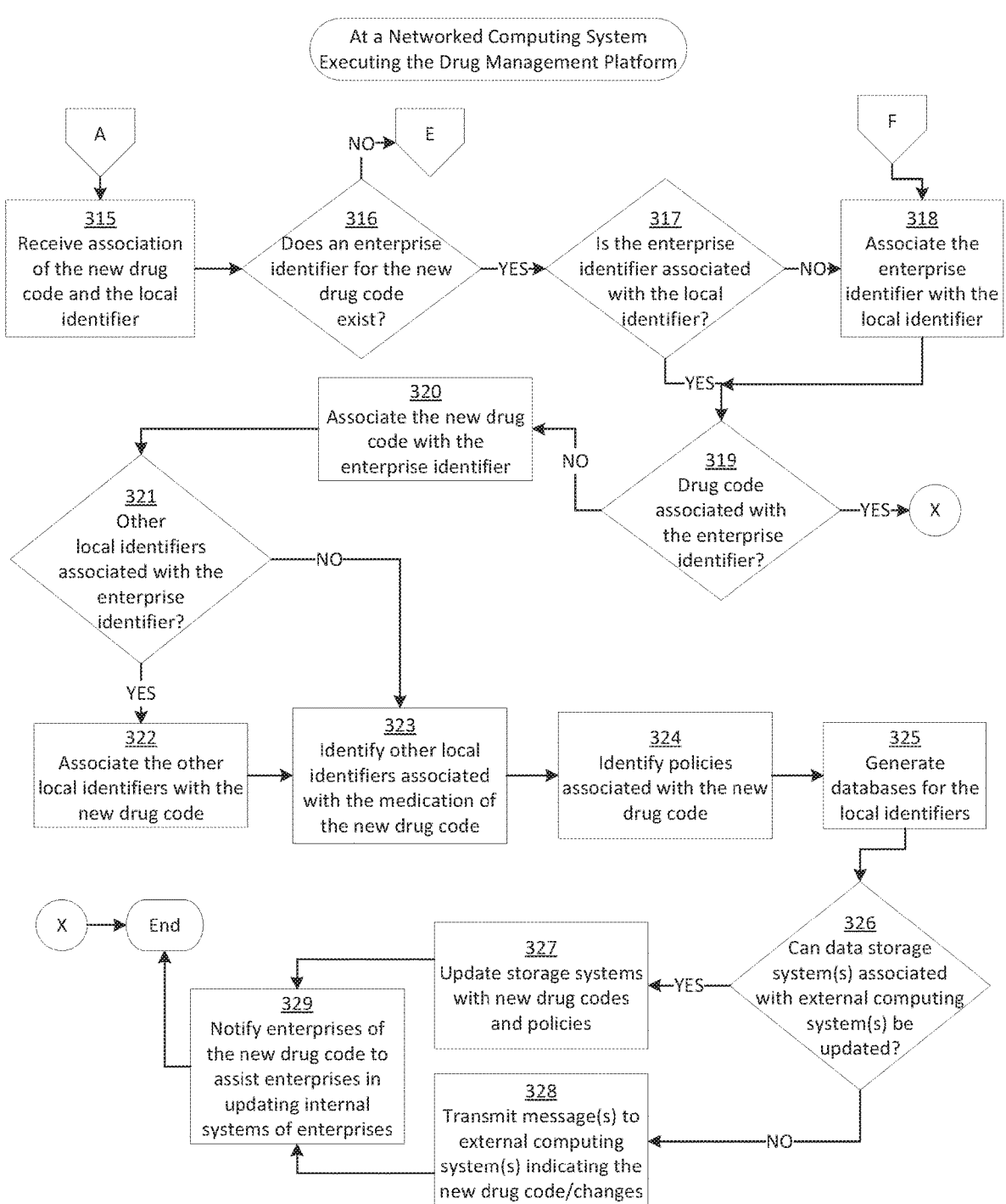
Figure 3D:
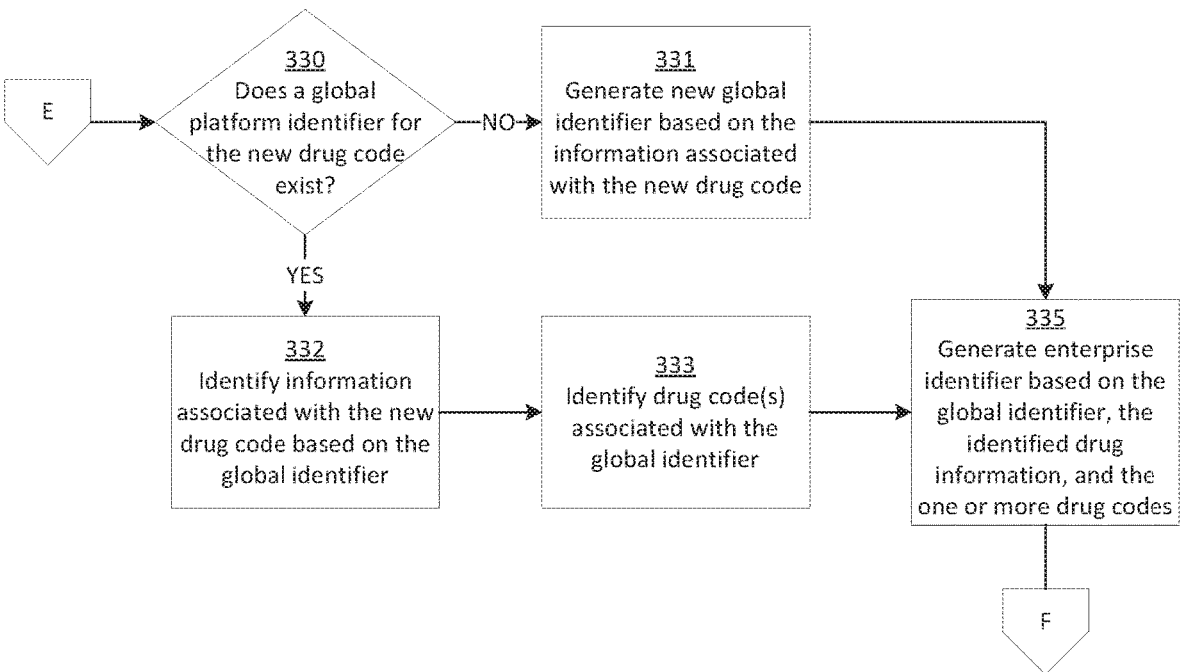

Turning now to FIG. 2, there is shown a block diagram depicting a networked computer system 108 in accordance with some implementations. The networked computer system 108 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. In some implementations, the networked computer system 108 may include a display device 212. In some implementations, the networked computer system 108 may include input devices such as a keyboard, a mouse, a trackpad, optical scanner, and/or input buttons. In some implementations, the display device 212 may include a touch-sensitive surface, in which case the display is a touch-sensitive display.

The memory 206 may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 206 includes one or more storage devices remotely located from the processor(s) 202. The memory 206, or alternatively the non-volatile memory device(s) within the memory 206, includes a non-transitory computer-readable storage medium. In some implementations, the memory 206 or the computer-readable storage medium of the memory 206 stores programs, modules, and/or data structures to be executed by one or more processors 202 for performing one or more operations of the networked computer system 108, and/or the techniques of the drug management platform 101 and of the optimization of drug management described herein. For example, the memory 206 may include programs, modules, and/or data structures for an operating system 226, a communication module 228, an access module 230, drug management platform instance 240, message module 232, local identifier module 234, drug configuration module 236, database generator module 238.

In some implementations, the operating system 226 module may include procedures for handling various basic system services and for performing hardware dependent tasks. The network communication module 228 may be configured for connecting the networked computer system 108 to other computing devices via the one or more communication network interfaces 204 (wired or wireless) and one or more communication networks 106. The access module 230 may be configured to grant, deny, and/or modify access to the networked computer system 108 and/or one or other computing systems or devices communicatively coupled to the networked computer system 108. The drug management platform instance module 240 may be configured to launch an instance of the drug management platform 101 on the networked computer system 108, and present any application user interfaces, such as graphical user interfaces (GUI) of the drug management platform 101. The drug management platform 101 may include various sub-units and/or modules, such as the message module 232, local identifier module 234, drug configuration module 236, database generator module 238, parser module 242, verification module 244.

The drug data management module 246 may be configured to create, store, update, verify, and/or maintain, drug data of drug management platform 101 in one or more databases, and/or other data structures within one or more data storage units (not shown separately) communicatively coupled to the networked computer system 108. Such drug data may include, but is not limited to, drug information, drug codes, predetermined medication, and the like, of the drugs identified and/or used within medical facilities. For example, such drug data may include drugs and/or medications used by at respective facilities associated with individual computing systems 102, 103, or 104. Each drug and/or medication used at a facility may be associated with one or more identifiers used in a computing systems, such as computing systems 102, 103, 104, and/or local health administration systems 105, 106, 107. As described above, such identifiers may be referred to herein as "local identifiers".

As described above, each facility may have multiple local identifiers for a single drug. For example, for Motrin 200 mg capsule, local health administration system 105*a* may have a first unique local identifier (e.g. Ax07), local health administration system 105*b* may have a second unique local identifier (e.g., PXR00c2), and local health administration system 105*c* may have a third unique local identifier (e.g., Rx200CM). Continuing with the preceding example, the drug data management module 246 may be configured to store the drug information of Motrin 200 mg capsule and associate the three different local identifiers of computing system 102 with the drug information of Motrin 200 mg capsule.

The drug data management module 246 may be configured to generate unique drug management platform 101 identifiers, as described above, referred to herein as "platform identifiers," for each drug stored in the one or more data storage units. The drug data management module 246 may be configured to store any predetermined medication for a drug in one or more data storage units communicatively coupled to the networked computer system 108, and associate the platform identifier with the predetermined medication. The drug data management module 246 may be configured to store drug information of a drug or a drug code, and associate the drug information with the platform identifier. The drug data management module 246 may be configured to associate the platform identifier of a drug with all the local identifiers of the drug. For example, using the identifiers and the drug of the preceding example, if the platform identifier for the drug Motrin 200 mg capsule is "BDMx200," the drug data management module 246 associates the platform identifier, RDMx200, with the local identifiers Ax07, PXR00c2, and Rx200CM. Similarly, the drug data management module 246 may associate the local identifiers of all the facilities associated with the drug management platform 101 with the platform identifier for Motrin 200 mg capsule.

The message module 232 may be configured to determine a type of the message received from a computing system of a facility, such as computing systems 102, 103, 104, local health administration systems 105, 106, 107, and the like. In some implementations, the received message may include one or more flags or type identifiers that indicate a type of message. The message module 232 may be configured to determine the message type based on the values of the one or more flags or type identifiers. In some implementations, the message may include a computing system identification information of a source of the message (e.g., name, address, device identifier, location coordinates). The message module 232 may determine a facility associated with the computing system, based on, for example, a mapping between computing system identification information and facilities. In some implementations, the message may include facility identification information (e.g., a unique identifier), and the message module 232 may be configured to determine the facility based on the facility identification information. In some implementations, the message module 232 may be configured to transfer messages to a computing system, such as computing system 102, 103, 104.

The local identifier module 234 may be configured to determine and/or identify local identifiers for the facilities associated with the drug management platform 101. The received message may include a local identifier within a first computing system of a facility that first identified the new drug code, (e.g., computing system 102), and with which that local identifier is associated. The local identifier module 234 may be configured to verify whether the local identifier received in a message exists within the drug data maintained by the drug data management module 246. In some implementations, if the local identifier module 234 determines that the local identifier does not exist, then the local identifier module 234 may be configured to add the local identifier to the drug data maintained by the drug data management module 246.

The parser module 242 may be configured to parse information related to, and/or associated with a new drug code received in the message. As described above, such information may be referred to herein as drug information. As described above, examples of such information include, but is not limited to, information related to a labeler (e.g., manufacturer, repackager, distributer, and the like), information related to a specific strength, dosage form (i.e., capsule, tablet, liquid, and the like), and/or formulation of the drug, information related to a type (e.g., capsule, tablet, liquid, and the like), and/or package size (e.g., 100 capsules) of the drug. The drug information of the new drug code may be received from a computing system of a facility, such as computing systems 102, 103, 104, local health administration systems 105, 106, 107, and the like. In some implementations, the drug information of the new drug code may be received in a message from a computing system of a facility and indicate an association with the new drug code. For example, the drug information may be received in the same message that includes the new drug code.

The drug configuration module 236 may be configured to identify one or more drugs within the drug data of the drug management platform 101 based on drug information of a new drug code, and/or the local identifier associated with the new drug code. In some implementations, the drug configuration module 236 may be configured to identify a drug within the drug data of the drug management platform 101 using a sequence of rules, and/or mapping algorithms, and based on the drug information of the new drug code. In some implementations, the drug configuration module 236 may be configured to utilize one or more machine learned models, which are trained to identify drugs from the drug data of the drug management platform 101 based on drug information of the new drug code. In some implementations, the drug configuration module 236 may be configured to determine one or more policies to associate with the new drug code based on the drug information of the new drug code and the drug data of the drug management platform 101. In some implementations, such policies may specify various rules that indicate how to store and/or administer certain drugs, and the like. For example, a policy may have rules that specify a type of drug storage cabinets for drugs that may be highly addictive (e.g., certain painkiller drugs).

The verification module 244 determines whether a local identifier associated with a new drug code is a correct local identifier. In some implementations, the verification module 244 may be configured to determine whether the associated local identifier is the correct local identifier based on data related to the new drug code (e.g., drug information of the new drug code) and the drug information associated with a platform identifier with which the local identifier associated with the new drug code is also associated. In some implementations, the verification module 244 may be configured to determine a platform identifier from the drug data of the drug management platform 101 based on the drug information associated with the new drug code. The verification module 244 may be configured to determine whether the local identifier associated with the new drug code is associated with the platform identifier. In some implementations, if the local identifier is not associated with the platform identifier, then the verification module determines that the association of the new drug code with the local identifier is not a correct association. In some implementations, if the local identifier is associated with the platform identifier, then the verification module determines that the association of the new drug code with the local identifier is a correct association.

In some implementations, the verification module 244 may be configured to cause presentation of one or more GUIs on a display device communicatively coupled to the networked computer system 108, such as the display 212. In some implementations, the one or more GUIs indicate to a user, such as an administrator of the drug management platform 101, whether the association of the received local identifier with the new drug code is correct. The one or more GUIs may be include one or more control elements to receive inputs from a user. Based on the received inputs from the user, the verification module 244 may be configured to create a new association between the new drug code and a new local identifier, and store the new association, or store the current association between the received local identifier and the new drug code, and/or store data that indicates that the user confirmed that the association between the received local identifier and the new drug code is accurate.

For example, if the verification module 244 determines that the association between the new drug code and the received associated local identifier is not accurate, then the verification module 244 may present GUIs to the user indicating that the association is not accurate or appears to be inaccurate (e.g., using a color designation or predefined flag). In response, the user may provide inputs to associate the new drug code with a new local identifier of that facility, then the verification module 244 may create a new association between the new drug code and the new local identifier and store the new association.

Similarly, if the verification module 244 determines that the association between the new drug code and the received associated local identifier is accurate or appears to be accurate, then the verification module 244 may present GUIs to the user indicating that the association is accurate or appears to be accurate (e.g., using a color designation or predefined flag). In response, the user may provide inputs confirming that the new drug code is correctly associated to the received local identifier, then the verification module 244 may store the association, and/or store data that indicates that the user confirmed that the association is accurate.

The database generator module 238 may be configured to generate one or more database entries, database tables, and/or other data structures, that may comprise the new drug code, drug information of the new drug code, policies, and/or local identifiers that are associated with the new drug code. In some implementations, the database generator module 238 may be configured to generate different database entries, tables, or data structures for each of the local identifiers. In some implementations, the database generator module 238 may be configured to grant access to a database entry, table, and/or other data structure based on the facility that has the local identifier. In some implementations, the database generator module 238 may be configured to generate temporary database entries, tables, and/or other data structures and provide access to computing systems based on facility identification information, computing system identification information, and/or local identifier information.

The above identified modules and applications may correspond to a set of executable instructions for performing one or more functions as described above and/or in the methods described in this application (e.g., the computer-implemented methods and other information processing methods described herein). One or more of the modules may be implemented as a specific hardware device with the appropriate input and output signal paths. The modules may be combined or otherwise re-arranged in various implementations. In some implementations, the memory 206 stores a subset of the modules and data structures identified above. In some implementations, the memory 206 stores additional modules and data structures not described above. Processors 202 may be configured to execute the above identified modules for performing the one or more above-described functions and/or techniques of optimized management of drugs at various computing systems of various facilities as described herein with reference to FIGS. 3A-3D.

Turning now to FIGS. 3A-3D, there is shown a flowchart illustrating an optimized process of managing drugs at various computing systems of various facilities and/or enterprises associated with a drug management platform. For the purpose of illustrating a clear example, components of the computing systems 102, 103, 104, and local health administration systems 105, 106, 107, shown and described with reference to FIG. 1, along with components of the networked computing system 108, shown and described with reference to FIGS. 1 and 2, may be used to describe the optimized process of managing drugs across various computing system of various facilities. In some implementations, the facilities may be independent or may be instances of a larger healthcare provider network. The process may be performed under control of one or more coordination devices which may be implemented in whole or in part by one or more of the systems described.

The method 300 includes receiving a new drug code (block 301), for example, at a local health administration system 105, 106, 107 and/or a computing system 102, 103, 104. The new drug code may be received via an input from a user of the local health administration system 105, 106, 107, and/or a computing system 102, 103, 104, such as a pharmacy technician. The local health administration system 105, 106, 107, and/or the computing system 102, 103, 104 transmits the new drug code to the drug management platform executed at a computing system, such as the networked computing system 108, to query the drug management platform for a local identifier associated with the drug code (block 302). In some implementations, the local health administration system 105, 106, 107, and/or the computing system 102, 103, 104 may be configured to transmit the drug code via a message specifying medication information associated with the drug code.

The networked computing system 108 executing the drug management platform 101 receives the new drug code (block 303). In some implementations, the new drug code may be received in a message from a computing system of a facility, such as the computing systems 102, 103, 104, local health administration systems 105, 106, 107, and the like. As described above, in some implementations, the processors

202 may be configured to determine whether the received message is for a new drug code (e.g., via the message module 232) based on data related to message type identifier tags or other flags that indicate a type of the message. The processor 202 determines whether the new drug code is known by the drug management platform 101 (block 304). In some implementations, the processor 202 may be configured to search the one or more data storage systems associated with the drug management platform 101 to determine whether the drug management 101 knows or is aware of the new drug code. If the processor 202 identifies the received new drug code in the one or more associated data storage systems, then the processor 202 may determine that the drug management platform 101 knows or is aware of the received new drug code. In some implementations, the processor 202 may determine whether the new drug code is known based on information associated with the new drug code and information associated with one or more drug codes stored in the one or more data storage systems associated with the drug management platform 101.

As described above, while a drug code may be a new or unknown to a system of a facility, the networked computing system 108 executing the drug management platform 101 may have received that drug code from a different system of that customer and/or enterprise or from a system of another customer and/or enterprise of the drug management platform 101, and the processor 202 may store the received drug code in association with information related to the drug code (e.g., information related to drug, medication, dispensable, infusible, product, package of the drug code) in one or more data storage systems associated with the drug management platform 101.

In some implementations, a new drug code may be for a new instance of a medication stored in drug management platform 101, where information related to one or more of drug, medication, dispensable, infusible, product, and/or package of the new instance of medication may be the same as the previous instance of the medication. The processor 202 may determine whether the new drug code is known by the drug management platform 101 based on a comparison of the information related to drug, medication, dispensable, infusible, product, and/or package of the new drug code with the corresponding information stored in association with the drug codes in the one or more data storage systems associated with the drug management platform 101. In some implementations, based on the comparison, the processor 202 may generate a value (e.g., a probability value) that indicates a likelihood of whether a drug code is known by the drug management platform 101, and the processor 202 may be configured to determine that the drug code is known by the drug management platform 101 if the value is above a threshold value.

If the processor 202 determines that the drug management platform 101 knows or is aware of the new drug code, then the method 300 proceeds to block 305. The processor 202 identifies a local identifier and transmits the local identifier to the computing system that transmitted the new drug code to cause that system to associate the identified local identifier to the new drug code (block 305). The processor 202 may identify the local identifier associated with a previous instance of the medication for which the new drug code is received. For example, as described above, if the processor 202 determines that the new drug code is for a new instance of a medication, then the processor 202 may identify the local identifier associated with the previous instance of the medication and send that local identifier to the computing system that sent the new drug code, such as the local health administration system 105, 106, 107 and/or computing systems 102, 103, 104.

As described above, a local identifier associated with a drug code may be an identifier of a system of an enterprise or a facility, such as the local health administration systems 105, 106, 107 and/or a computing system 102, 103, 104, and the processor 202 may identify the local identifier of the drug code based on the association between the drug code and the local identifier. In some implementations, a drug code may be stored in association with an enterprise master identifier and a local identifier. The enterprise master identifier may be associated with one or more local identifiers for each drug code associated with the enterprise master identifier. The enterprise master identifier may be associated with one or more computing systems of a facility and/or enterprise, such as the local health administration systems 105, 106, 107, and/or a computing system 102, 103, 104, via the identifiers of each of one or more computing systems of a facility and/or an enterprise, and the enterprise master identifier In some implementations, each enterprise master identifier may be stored in association with an identifier of each of the one or more systems of a facility and/or an enterprise, such as the local health administration systems 105, 106, 107, and/or a computing system 102, 103, 104. The processor 202 may receive an identifier of a system and the enterprise master identifier associated with the system from the system sending the drug code, and the processor 202 may identify a local identifier for that system based on the associations between the identifier of the system sending the drug code, the enterprise master identifier, the drug codes, and the local identifiers. The computing system of the facility and/or enterprise receives the local identifier from the networked computing system 108 (block 307). The computing system of the facility associates the new drug code with the received local identifier (block 308). The computing system of the facility stores the received local identifier in association with the new drug code in a storage system associated with the computing system of the facility. The computing system of the facility notifies the association of the new drug code and the local identifier to the drug management platform 101 by sending the association of the new drug code and the local identifier to the networked computing system 108 (block 309). The method 300 then proceeds to block 315.

Returning to block 304, if the processor 202 determines that networked computing system 108 determines that the new drug code is not known by the drug management platform 101 ('NO' at block 304), then the method 300 proceeds to block 306. The processor 202 transmits a message to the computing system that transmitted the new drug code indicating that the drug management platform 101 does not know the new drug code (block 306). The computing system of the facility receives the message indicating that the new drug code is not known (block 310). The computing system of the facility identifies information associated with the new drug code (block 311) and generates a new local identifier for the new drug code based on the identified information (block 312). The computing system of the facility associates the local identifier with the new drug code (block 313). The computing system of the facility may store the local identifier in association with the new drug code. In some implementations, as shown in block 314, the computing system of the facility may determine whether the association of the local identifier to the new drug code is accurate based on rules and/or preferences for local identifiers for that computing system. If the computing system determines that the association is not accurate ('NO' at block 314), then the computing system of the facility generates a new local identifier (block 312). If the computing system of the facility determines that the association is accurate ('YES' at block 314), then the computing system of the facility transmits the association of the new drug code and local identifier to the drug management platform (block 309). The method proceeds to block 315.

The processor 202 of the networked computing system 108 executing the drug management platform 101 receives association of the new drug code and the local identifier (block 315). In some implementations, the processor 202 may determine whether the received association between the new drug code and the local identifier is accurate. The processor 202, for example, via the verification module 244, may be configured to determine whether the association of the new drug code with the local identifier is accurate. For example, the processor 202 may determine that the association between the new drug code and the local identifier is inaccurate if the local identifier is associated with a different drug code with different drug concept, medication concept, dispensable concept, and/or infusible concept information than the new drug code. In some implementations, the processor 202 may cause presentation of GUIs, or other user interfaces, or prompts to a user, such as an administrator of the drug management platform 101 (e.g., via the verification module 244) to verify accuracy of the association between the drug code and the local identifier. The processor 202, for example via the verification module 244, may be configured to cause presentation of GUIs, or other user interfaces, or prompts, indicating that the association is accurate or inaccurate.

If the user provides an input that the association is inaccurate, the processor 202, for example, via the verification module 244, may be configured to mark the association between the new drug code and the local identifier as inaccurate. If the user provides an input that the association is accurate, the processor 202, for example, via the verification module 244, may be configured to store the current association between the local identifier and the new drug code, and/or store data that indicates that the user confirmed that the association between the local identifier and the new drug code is accurate in a data storage unit communicatively coupled to the networked computer system 108, such as the data storage unit storing the drug data of the drug management platform 101. In some implementations, the processor 202 may transmit information to the computing system of the facility indicating that the received association between the local identifier and the new drug code is inaccurate. In some implementations, the processor 202 may receive a new association between the new drug code and a new local identifier from the computing system of the facility, and the processor 202 may verify whether new association is accurate. In some implementations, the processor 202 may be configured to verify whether the association between the new drug code and the local identifier is accurate for a predetermined number of times and transmit an error message to the local computing system if the number of attempts of verifying the association exceeds the predetermined number.

After the processor 202 confirms that the association between the local identifier and the new drug code is accurate, then the method proceeds to block 316. The processor 202 determines whether an enterprise identifier for the new drug code exists (block 316). As described above, an enterprise identifier may be a unique identifier for a drug code for an enterprise or customer of the drug management platform, and the enterprise identifier may be stored in association with a corresponding drug code, one or more local identifiers for the drug code, and/or at least some information related to the drug code (e.g., drug concept, medication concept, dispensable concept, infusible concept, product, and/or package). In some implementations, the processor 202 may determine whether the drug code is for a new instance of a medication which the drug management platform 101 is aware of based on the information related to the new drug code and the information stored in association with drug codes that the drug management platform is aware of. If the processor 202 determines that the new drug code for a new instance of a medication which the drug management platform is aware of, then the processor 202 may identify the enterprise identifier of the previous instance of the medication as the enterprise identifier for the new drug code and determine that the enterprise identifier exists for the new drug code. In some implementation, the processor 202 may search one or more data storage units associated with the drug management platform 101 for the new drug code, and determine that the enterprise identifier exists if an enterprise identifier is stored in association with the new drug code.

If the processor 202 determines that the enterprise identifier for the new drug code does not exist ('NO' at block 316), then the method proceeds to block 330. The processor 202 determines whether global platform identifier exists for the new drug code (block 330). As described above, the global platform identifier may be a unique identifier for a drug code, and may be stored in association with the drug code, the information related to the drug code (e.g., information related to drug concept, medication concept, dispensable concept, infusible concept, product, and/or package), and/or the one or more enterprise identifiers, where each enterprise identifier may be an identifier for the drug code for an enterprise and/or a customer of the drug management platform 101. The processor 202 may search one or more data storage units associated with the drug management platform 101 for the new drug code and/or information related to the new drug code, and determine that a global platform identifier exists if a global platform identifier is stored in association with the new drug code or with drug codes that have the same information as the new drug code.

If the processor 202 determines that the global platform identifier for the new drug code exists ('YES' at block 330), then the method proceeds to block 332. The processor 202 identifies the drug information associated with the new drug code based on the global platform identifier (block 332). The processor 202 identifies one or more drug codes associated with the global platform identifier (block 333), If the processor 202 determines that the global platform identifier for new drug code does not exist ('NO' at block 330), then the method proceeds to block 331. The processor 202 generates a new global identifier based on the information associated with the new drug code (block 331). The processor 202 generates an enterprise identifier based on the global platform identifier, the information associated with the new drug code, and drug codes, if any, associated with the global platform identifier (block 335). The processor 202 may store the generated enterprise identifier in association with the global platform identifier, the identified drug information, and drug codes in one or more data storage units associated with the drug management platform 101. The method proceeds to block 318.

Returning to block 316, if the processor 202 determines that the enterprise identifier for the new drug code exists ('YES' at block 316), then the method 300 proceeds to block 317. The processor 202 determines whether the enterprise identifier is associated with the local identifier (block 317). The processor 202 may search one or more data storage units associated with the drug management platform 101 for the local identifier associated with the new drug code, and determine that the local identifier is associated with the enterprise identifier if the local identifier is stored in association with the enterprise identifier, lithe processor 202 determines that the enterprise identifier is not associated with the local identifier ('NO' at block 317), then the method 300 proceeds to block 318. The processor 202 associates the enterprise identifier with the local identifier (block 318). The processor 202 stores the local identifier in association with the enterprise identifier in one or more data storage units associated with the drug management platform 101. The method 300 proceeds to block 319.

If the processor 202 determines that the enterprise identifier is associated with the local identifier ('YES' at block 317), then the method proceeds to block 319. The processor 202 determines whether the new drug code is associated with the enterprise identifier (block 319). The processor 202 may search for the enterprise identifier in one or more data storage units associated with the drug management platform 101 and determine that the new drug code is associated with the enterprise identifier if the drug code is stored in association with the enterprise identifier. If the processor 202 determines that the enterprise identifier is associated with the new drug code ('YES' at block 319), then the method 300 terminates. If the processor 202 determines that the enterprise identifier is not associated with the local identifier ('NO' at block 319), then method proceeds to block 320.

The processor 202 associates the new drug code with the enterprise identifier (block 320). The processor 202 may store the new drug code in association with the enterprise identifier in one or more data storage units associated with the drug management platform 101. The processor 202 determines whether any other local identifiers are associated with the enterprise identifier (block 321). The other local identifiers associated with the enterprise identifier may be local identifiers of other computing systems of an enterprise and/or a customer of the drug management platform 101. If the processor 202 determines that other local identifiers are associated with the enterprise identifier ('YES' at block 321), then the method 300 proceeds to block 322. The processor 202 associates the other local identifiers with the new drug code (block 322). If the processor 202 determines that no other local identifiers are associated with the enterprise identifier ('NO' at block 321). The method 300 proceeds to block 323.

The processor 202 identifies local identifiers of other enterprises and/or customers of the drug management platform 101 based on the medication information of the new drug code (block 323). The processor 202 associates the other identified local identifiers of the other enterprises and/or customers with the new drug code and stores the association in one or more data storage units associated with the drug management platform 101. The processor 202 identifies policies associated with the medication of the new drug code (block 324). Policies for medications may be stored in association with the local identifiers and information associated with drug codes of the local identifiers in one or more data storage units associated with the drug management platform 101. The processor 202 may generate databases for the local identifiers (block 325). The processor 202 may be configured to generate databases with the local identifiers, the new drug code, and any policies to associate the new drug code in the computing systems 102, 103, 104 and/or local health administration systems 105, 106, 107. The processor 202 may be configured to generate temporary or secondary databases for the computing systems of the customers, enterprises and/or facilities whose local identifiers are being associated with the new drug code. In some implementations, processor 202 may grant access to the computing systems of the customers, enterprises and/or facilities for certain temporary databases based on the local identifiers associated with the facilities. In some implementations, the processor 202 may be configured to grant access to the facilities for certain temporary databases by creating and/or specifying application programming interfaces (APIs) to connect to the temporary databases, and providing the application programming interfaces to the facilities (e.g., via a network interface). Additionally or in the alternative, the processor 202 may be configured to grant access to the facilities for certain temporary databases by causing the presentation of a graphic user interface (e.g., via one or more webpages provided over a network), to allow a user, such as an administrator of the drug management platform 101, to provide inputs granting access to the facilities for the temporary databases.

The processor 202 determines whether one or more data storage systems associated with computing systems of a facility and/or an enterprise can be updated automatically (block 326). In some implementations, the processor 202 may determine whether a data storage system of a facility can be automatically updated based on mapping of access grants and/or rules to the data storage systems of the facilities that indicate whether a data storage system can be updated automatically. In some implementations, the mapping may be provided in a hierarchy whereby the location of a source of an update within the hierarchy is compared to a receiving facility's location. If the source is located closer to the root node of the hierarchy, the update may be accepted. If the source is at the same level or below the receiving facility, the update may be received and identified for further review without automatic updating. A rule may be based on the source, drug, drug type (e.g., classification), manufacturer, or other information associated with the update or facilities.

If the processor 202 determines that the facility data storage system cannot be updated automatically ('NO' at block 326), the method 300 proceeds to block 328. The processor 202 transmits one or more messages to the computing system (e.g., computing system 102) indicating new drug code and/or changes (block 328), The message may be an alert to the computing system or a user of the computing system that a new drug code is to be associated with one or more local identifiers. In some implementations, the processor 202 may transmit the message to a computing system of a facility, such as computing systems 102, 103, 104, local health administration systems 105, 106, 107, and the like, via one or more APIs implemented by the computing system of the facility. The message may include information to establish a connection between a data store and the computing system to store the local identifier, or may include the association and/or mapping between the drug code and a local identifier. The method 300 proceeds to block 329.

If the processor 202 determines that the facility data storage system can be updated automatically ('YES' at block 326), the method 300 proceeds to block 327. The processor 202 updates the data storage system of the facility with the new drug code (block 327). In some implementations, the processor 202 may be configured to generate a data storage system object (e.g., a database entry) and update the data storage system of the facility with the generated data storage system object. In some implementations, the update may include indexing at least a portion of the data storage system to expedite identification of records by drug code and/or local identifiers. The processor 202 transmits one or more messages to the enterprises to assist enterprises in updating one or more internal systems of the drug management platform 101 (block 329).

In some implementations, a computing system may transmit a local identifier for a drug that appears (to the computing system) to be a new drug. However, the drug may be known to another at a facility associated with a different computing system or to the drug management platform 101. In such instances, the drug management platform 101 may identify a handling configuration for the drug and transmit control messages to the computing system for configuring hardware used to process the drug. The handling configuration may be stored in a data store accessible by the drug management platform 101 in association with identifying information for the drug. For example, the drug may be a temperature controlled substance. In such instances, the drug management platform 101, upon receiving a message from the computing system indicating receipt of a "new" drug, may transmit a refrigeration control message for configuring a refrigeration unit at the medical facility. Other examples of handling configuration control messages include locking/ unlocking protocols such as for accessing controlled substance storage locations (e.g., cabinets, bins, rooms), waste device protocol (e.g., empty to drain, empty to hazardous container, isolated waste, witnessing requirements), or the like.

The features described provide a variety of technical advantages in the field of medication management. One non-limiting advantage is to ensure the consistency of codes across facilities. In some instances, there may be hundreds of different health care organizations each with multiple facilities. In some cases, each facility may manage its own library of codes which may be different from other facilities within the health care organization and/or across all health care organizations.

Some solutions include a periodic consultation with a published authoritative source of harmonized drug codes. However, this source is updated at a rate that is slower than the rate at which items are received at a facility. Accordingly, when a pharmacy receives an item that has not previously been received, arbitrary and unverified information may be associated with the new item. This information quickly spreads throughout health information systems such as medical records, billing, inventory, preparation, dispensing, etc. which may each have their own corresponding code and data store. Once available, ensuring the information is accurately reflected throughout the enterprise can be resource intensive.

In addition to updating the information, there is also little quality control over the entered information for the item. In some instances, manual or semi-automated systems may be used to receive input information for the item. This process is typically free format input and can be prone to errors such as entering the wrong dose amount, wrong dose counts, misspelling item names, item manufacturer names, or lot codes, wrong expiration date, wrong handling parameters (e.g., temperature), etc.

The features described provide a consistent and verifiable system and method to address these and other challenges.

Example Embodiments

Consider a system with three levels of identifiers for items. One level may be referred to as the global level. This may be a conceptual medication taxonomy that live above any individual customer and designed to be able to produce taxonomic data in any format for consumption by any arbitrary customer enterprise. This top layer supports crowd-sourcing, global data enrichment, and support for cross-facility analytics. It is a drug management platform such described in FIG. 1 that can be connected to each facilities' computing system (e.g., drug management platforms), and serves as a reliable source of already-known medication data.

The second level generally relates to an enterprise business entity consisting of a variety of facilities (e.g., hospitals, clinics, medical office buildings, infusion centers, long-term care sites, etc.) that maintains its own drug management platform for consumption by the entities it owns. Using its own drug management platform, an enterprise entity may share information among its facilities. The drug management platform can additionally create 'standards' by which it can enforce certain processing rules for specific medication across all the facilities it owns or controls. So, for example, the drug management platform at the enterprise level (or at the regional level—for very large enterprises) may assert that medication dispensing cabinets used within the enterprise all use exactly the same rules and workflows to manage controlled substances, such as opiates The third level may be referred to as a facility. A facility represents a site of an enterprise that has an instance of an electronic medical record system (EMR) and one or more instances of medication management systems. Multiple facilities can share one instance of an EMR. In some cases, a facility may have multiple EMR systems, especially if some services, like Emergency Departments, are outsourced. While some medication management systems can interface to multiple EMR's, for practical purposes, each of those interfaces is a silo that effectively operates as a separate facility.

In general, the suite of medication management systems in place within a facility interfaces directly with a single instance of an EMR. In that interface the EMR is the source of encoding (e.g., a local identifier). When a new medication is introduced, it is generally first seen at the facility level, typically as the result of a purchase of that new medication. That instantiation of a new medication typically first appears in that facility's EMR. The resulting encoding (e.g., local identifier) may then be used to describe that medication in the medication management system(s) for that facility.

Medications at all three layers can be characterized using an item code. In the US, an item code may be included in a collection of national drug codes (NDC's) each of which specifies a unique packaging of a specific manufacturer's instance of a medication. Some jurisdictions require that each instance of a medication be labeled with its NDC both in human-readable form and in a barcode that represents the NDC.

In some instances, the only portion of the item code that is defined by the entity controlling the collection of codes (e.g., the Food and Drug Administration in the United States) is the portion of the item code assigned to the manufacturer. Other portions of the item code can be used by the manufacturer according to their needs. For example, U.S. NDC codes may include two additional portions that describe the medication and the packaging. When the item is introduced to the market, these portions are created by the manufacturer and applied to the new items. One result of such systems is that the codes appearing on items can change frequently and without warning. Indeed, the most frequent changes to the formularies of EMR's and medication management systems is the augmentation of the list of NDC's associated with a medication. By corollary, the single most frequent error associated with the manual maintenance of formularies of medication is the manual association of an NDC to the wrong medication.

The features described detect new NDC's when items are received into inventory. For example, when a new and unknown NDC is received into inventory, it may be unknown only to that facility—EMR pair, or it may be generally unknown.

The receiving system may first query an enterprise data management platform, and then the global enterprise management platform to see if the NDC is, in fact, known to exist. If it does exist, then the medication management system can acquire the local identifier of the medication the NDC represents, and presents the description of the medication and its local identifier to the user. In some systems, the information may be verified using machine learning or through user inspection via a GUI. If the user is authorized to verify the match, then they do so by affirming that the new NDC should be associated with the proposed local identifier.

If the NDC is completely unknown, then the user of the affected medication management system can manually add the NDC to the appropriate medication record. This addition may be using one or more of barcode scanning, image recognition, or a GUI. To avoid errors, double-checks can be associated with the addition procedure. For example, the edit to the NDC list of the medication may be received by the enterprise drug management system, where it is again reviewed. If an error or discrepancy is found between the entered information and the current record at the enterprise level, the originating system is may be corrected and resubmitted for local processing. If no error is identified, the enterprise data management system may determine the local identifier(s) for each of the local system(s) and uses each identifier to update the NDC list for the appropriate medication in each of the local medication management systems.

When adding a new medication to such ecosystems, the process typically includes adding medication to a formulary (e.g., a list of permitted medications) at the facility level. Ultimately, because the encoding of the new medication(s) comes from each EMR system at each facility, to ensure integrity of the information systems, additions should occur first in the EMR and then propagate to the medication management system(s) served by the EMR. To the extent that a single system of medication management systems serves multiple facilities served by the same instance of an EMR, that process may be simplified using at least some of the features described, since one change occurs simultaneously for the each of the served systems.

The addition of a new medication for the first time according to this disclosure typically occurs within one of a plurality of medication management systems at a particular facility after it has been created in that facility's EMR, using the local encoding provided by that EMR. As part of that process, the collection of NDC's for that medication may also be determined and entered. Because this matching of NDC's can drive bedside medication safety systems (e.g., bar code medication administration—BCMA), the quality of that association is carefully governed and rapidly repaired if it is entered in error.

As a result of adding a new item to one system's formulary, the change can be published to the enterprise drug management platform where it is again reviewed. If errors in entry are discovered, they can be corrected in the originating system before further activity can occur. Entry into the enterprise drug management platform results in an enterprise identifier that, over time, normalizes all the individual local identifiers at all the facilities in the enterprise. As part of this process, an automated mapping algorithm can check the newly introduced medication against a global drug management platform. This check can verify the entry's identity, characteristics, and list of NBC's. The curator of the global drug management system may approve or reject the addition of any hitherto unknown medications to the global drug management system and supplies a global identifier back to the enterprise system.

Once entered and approved in the enterprise drug management system, the enterprise system may then publish the new medication to each facility for potential addition. At the originating system, the medication and its associated data may be published to other medication management systems used in that facility, containing the information needed for each such system. For other facilities with other EMR's, each facility may choose to add, or not add, the item to their local facility. The choice may be based on rules defining which, if any, update sources to accept. The choice may be based on a review of pending edits by an authorized user via a GUI. If addition occurs, then the facility may first generate a record for the medication in their EMR, acquire the local identifier from the EMR, and use it to accept the published information into each of their systems. If a facility originally declines to add the item to their local formulary, they can do so later by first creating it in their EMR and then pulling the medication information down from their enterprise drug management system.

In these cases, the mapping of NDC's to local, enterprise and, ultimately, global identifiers is a curated process driven by a matching algorithm that uses machine learning to improve its match predictions based on experience in matching previous items.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software, or any combination thereof.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A computer-implemented method of managing drug products, comprising: receiving, by a central computing system from a first client system, a new item code and drug information associated with the new item code; determining, by the central computing system based at least in part on the received drug information, a medication and a first local identifier used by the first client system to identify the medication; determining, by the central computing system based at least in part on identifying the first local identifier, one or more second local identifiers that identify the medication; identifying, by the central computing system, based at least in part on the one or more second local identifiers, a plurality of second client systems that use the one or more second local identifiers; and providing, by the central computing system, an instruction to each of the plurality of second client systems to associate, at the second client system, one or more corresponding second local identifiers with the new item code.

Clause 2. The method of Clause 1, further comprising: providing, before providing the instruction to each of the plurality of second client systems, the one or more second local identifiers and an indication of the plurality of second client systems to a user interface for confirmation by an administrator that the new item code should be associated with the one or more second local identifiers at the plurality of second client systems; receiving the confirmation; and providing the instruction in response to the confirmation.

Clause 3. The method of Clause 1, wherein the one or more corresponding second local identifiers are the local identifiers used at the second client system.

Clause 4. The method of Clause 3, wherein providing the instruction comprises automatically updating a data store within one or more of the second client systems with the association of the new item code with the one or more corresponding second local identifiers.

Clause 5. The method of Clause 3, further comprising: generating a data storage object for each association between a second local identifier of the one or more second local identifiers and the new item code, wherein the data storage object comprises the new item code and the second local identifier; and storing each of the generated data storage objects in a different data store.

Clause 6. The method of Clause 5, further comprising: determining, based at least in part on the second local identifier stored it the generated data storage object, a second client system of the plurality of second client systems; and granting access to the second client system for the data store storing the data storage object that comprises the second local identifier.

Clause 7. The method of Clause 1, further comprising: receiving, from the first client system, drug information related to the new item code; determining, based at least in part on the drug information, a platform identifier; and determining, based at least in part on the platform identifier, one or more second local identifiers when the first local identifier does not exist.

Clause 8. The method of Clause 1, further comprising: determining, based at least in part on the first local identifier, one or more third local identifiers when the first local identifier exists, wherein the one or more third local identifiers are used by the first client system; and providing an instruction to the first client system to associate the one or more third local identifiers with the new item code.

Clause 9. The method of Clause 1, wherein providing the instruction comprises: updating a data store with the association of the one or more corresponding second local identifiers with the new item code; and granting access to the plurality of second client systems to the data store for retrieval of the association by the plurality of second client systems.

Clause 10. The method of Clause 1, wherein the one or more second local identifiers determined based on a platform identifier associated with first local identifier.

Clause 11. A system, comprising: a memory storing instructions; and one or more processors coupled with the memory and configured to execute the instructions to cause the system to: receive, from a first client system, a new item code and drug information associated with the new item code; determine, based at least in part on the received drug information, a medication and a first local identifier used by the first client system to identify the medication; determine, based at least in part on identifying the first local identifier, one or more second local identifiers that identify the medication; identify, based at least in part on the one or more second local identifiers, a plurality of second client systems that use the one or more second local identifiers; and provide, an instruction to each of the plurality of second client systems to associate, at the second client system, one or more corresponding second local identifiers with the new item code.

Clause 12. The system of Clause 11, wherein the one or more processors are configured to execute instructions to cause the system to: provide, before providing the instruction to each of the plurality of second client systems, the one or more second local identifiers and an indication of the plurality of second client systems to a user interface for confirmation by an administrator that the new item code should be associated with the one or more second local identifiers at the plurality of second client systems; receive the confirmation; and provide the instruction in response to the confirmation.

Clause 13. The system of Clause 11, wherein the one or more corresponding second local identifiers are the local identifiers used at the second client system.

Clause 14. The system of Clause 13, wherein the one or more processors are configured to execute instructions to cause the system to: automatically update a data store within one or more of the second client systems with the association of the new item code with the one or more corresponding second local identifiers, when providing the instruction.

Clause 15. The system of Clause 13, wherein the one or more processors are configured to execute instructions to cause the system to: generate a data storage object for each association between a second local identifier of the one or more second local identifiers and the new item code, wherein the data storage object comprises the new item code and the second local identifier; and store each of the generated data storage objects in a different data store.

Clause 16. The system of Clause 15, wherein the one or more processors are configured to execute instructions to cause the system to: determine, based at least in part on the second local identifier stored it the generated data storage object, a second client system of the plurality of second client systems; and grant access to the second client system for the data store storing the data storage object that comprises the second local identifier.

Clause 17. The system of Clause 11, wherein the one or more processors are configured to execute instructions to cause the system to: receive, from the first client system, drug information related to the new drug code; determine, based at least in part on the drug information, a platform identifier; and determine, based at least in part on the platform identifier, one or more second local identifiers when the first local identifier does not exist.

Clause 18. The system of Clause 11, wherein the one or more processors are configured to execute instructions to cause the system to: determine, based at least in part on the first local identifier, one or more third local identifiers when the first local identifier exists, wherein the one or more third local identifiers are used by the first client system; and provide an instruction to the first client system to associate the one or more third local identifiers with the new item code.

Clause 19. The system of Clause 11, wherein the one or more processors are configured to execute instructions to cause the system to: update a data store with the association of the one or more corresponding second local identifiers with the new drug code; and grant access to the plurality of second client systems to the data store for retrieval of the association by the plurality of second client systems.

Clause 20, The system of Clause 11, wherein the one or more processors are configured to execute instructions to cause the system to: determine the one or more second local identifiers based on a platform identifier associated with first local identifier.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, hut, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A computer-implemented method of managing drug products across health administration systems, performed by a central computing system, comprising:

receiving a plurality of messages from a plurality of client systems via a network;

parsing the plurality of messages to identify a new item code in the plurality of messages;

receiving, at a first client system of the plurality of client systems, drug information associated with the new item code;

applying a machine-learned classification model to the drug information to identify a predetermined medication;

determining, based at least in part on the received drug information, a first local identifier used by the first client system to identify the predetermined medication;

determining that the first local identifier is not associated with the new item code based on the drug information associated with the new item code and a platform identifier with which the first local identifier is also associated or based on the first local identifier not being associated with a platform identifier;

causing, responsive to determining that the first local identifier is not associated with the new item code, presentation of a graphical user interface on a display device, including a prompt indicating an inaccurate association of the first local identifier and one or more control elements for receiving user input pertaining to an association between the new item code and respective local identifier;

receiving, via the one or more control elements of the graphical user interface, user input of one or more second local identifiers that identify the predetermined medication for association with the new item code;

based at least in in part on receiving the one or more second local identifiers:

identifying, based at least in part on the one or more second local identifiers, a plurality of second client systems;

generating one or more facility-specific temporary databases for storing records associated with the one or more second local identifiers and a new record of a new association between the one or more second local identifiers and the new item code, and for proposed updates to associations between the new item code and respective identifiers;

storing, in the one or more facility-specific temporary databases, data that indicates that a user confirmed that the new association between the one or more second local identifiers and the new item code is accurate;

granting access to the plurality of second client systems to the one or more facility-specific temporary databases via a web interface or an application programming interface (API) for retrieval of the new association and for verification and approval of the proposed updates by facility administrators of the plurality of second client systems; and automatically storing and indexing the proposed updates by item code and local identifier to enable rapid lookup at each client system;

providing, over the network, an instruction to each of the plurality of second client systems to associate, at the second client system, the one or more second local identifiers with the new item code;

receiving a message from a respective client system indicating receipt of the new item code;

identifying a handling configuration for configuring hardware used to process the predetermined medication corresponding to the new item code at a corresponding facility associated with the respective client system; and automatically transmitting, responsive to receiving the message indicating receipt of the new item code and identifying the handling configuration, a hardware control message to a hardware unit at the corresponding facility to cause an adjustment of the hardware unit according to predefined handling parameters.

2. The method of claim 1, further comprising:

providing, before providing the instruction to each of the plurality of second client systems, the one or more second local identifiers and an indication of the plurality of second client systems to the web interface for confirmation by an administrator that the new item code should be associated with the one or more second local identifiers at the plurality of second client systems;

receiving the confirmation;

storing data in the facility-specific temporary database that indicates that the administrator confirmed that the association between the local identifier and the new item code is accurate; and providing the instruction in response to the confirmation.

3. The method of claim 1, wherein the one or more second local identifiers are the local identifiers used at the second client system.

4. The method of claim 3, wherein providing the instruction comprises automatically updating a data store within one or more of the second client systems with the association of the new item code with the one or more second local identifiers.

5. The method of claim 3, further comprising:

generating a data storage object for each association between a second local identifier of the one or more second local identifiers and the new item code, wherein the data storage object comprises the new item code and the second local identifier; and storing each of the generated data storage objects in a different data store.

6. The method of claim 5, further comprising:

determining, based at least in part on the second local identifier stored it the generated data storage object, a second client system of the plurality of second client systems; and granting access to the second client system for a data store storing the data storage object that comprises the second local identifier.

7. The method of claim 1, further comprising:

receiving, from the first client system, drug information related to the new item code;

determining, based at least in part on the drug information, a platform identifier; and determining, based at least in part on the platform identifier, one or more second local identifiers when the first local identifier does not exist.

8. The method of claim 1, further comprising:

determining, based at least in part on the first local identifier, one or more third local identifiers when the first local identifier exists, wherein the one or more third local identifiers are used by the first client system; and providing an instruction to the first client system to associate the one or more third local identifiers with the new item code.

9. The method of claim 1, wherein the one or more second local identifiers are determined based on a platform identifier associated with first local identifier.

10. A system for managing drug products across health administration systems, comprising:

a memory storing instructions; and one or more processors coupled with the memory and configured to execute the instructions to cause the system to:

receiving a plurality of messages from a plurality of client systems via a network;

parse the plurality of messages to identify a new item code in the plurality of messages;

receive, at a first client system of the plurality of client systems, drug information associated with the new item code;

apply a machine-learned classification model to the drug information to identify a predetermined medication;

determine, based at least in part on the received drug information, a first local identifier used by the first client system to identify the predetermined medication;

determine that the first local identifier is not associated with the new item code based on the drug information associated with the new item code and a platform identifier with which the first local identifier is also associated or based on the first local identifier not being associated with a platform identifier;

cause, responsive to determining that the first local identifier is not associated with the new item code, presentation of a graphical user interface on a display device, including one or more control elements for receiving user input pertaining to an association between the new item code and respective local identifier;

receive, based at least in part on identifying the first local identifier, via the one or more control elements of the graphical user interface, user input of one or more second local identifiers that identify the predetermined medication for association with the new item code;

based at least in in part on receiving the one or more second local identifiers:

identify, based at least in part on the one or more second local identifiers, a plurality of second client systems;

generate a facility-specific temporary database that stores one or more records for the one or more second local identifiers and a new record of a new association between the one or more second local identifiers and the new item code, and for proposed updates to associations between the new item code and respective identifiers;

store, in the facility-specific temporary database, data that indicates that a user confirmed that the new association between the one or more second local identifiers and the new item code is accurate;

provide an instruction to the first client system to use the one or more second local identifiers for the new item code;

grant access to the plurality of second client systems to the facility-specific temporary database via a web interface or an application programming interface (API) for retrieval of the new association and for verification and approval of the proposed updates by facility administrators of the plurality of second client systems;

automatically store and index the proposed updates by item code and local identifier to enable rapid lookup at each client system;

provide, over the network, an instruction to each of the plurality of second client systems to associate, at the second client system, the one or more second local identifiers with the new item code receive a message from a respective client system indicating receipt of the new item code;

identify a handling configuration for configuring hardware used to process the predetermined medication corresponding to the new item code at a corresponding facility associated with the respective client system; and automatically transmit, responsive to receiving the message indicating receipt of the new item code and identifying the handling configuration, a hardware control message to a hardware unit at the corresponding facility to cause an adjustment of the hardware unit according to predefined handling parameters.

11. The system of claim 10, wherein the one or more processors are configured to execute instructions to cause the system to:

provide, before providing the instruction to each of the plurality of second client systems, the one or more second local identifiers and an indication of the plurality of second client systems to a user interface for confirmation by an administrator that the new item code should be associated with the one or more second local identifiers at the plurality of second client systems;

receive the confirmation;

store data in the facility-specific temporary database that indicates that the administrator confirmed that the association between the local identifier and the new item code is accurate; and provide the instruction in response to the confirmation.

12. The system of claim 10, wherein the one or more second local identifiers are the local identifiers used at the second client system.

13. The system of claim 12, wherein the one or more processors are configured to execute instructions to cause the system to:

automatically update a data store within one or more of the second client systems with the association of the new item code with the one or more second local identifiers, when providing the instruction.

14. The system of claim 12, wherein the one or more processors are configured to execute instructions to cause the system to:

generate a data storage object for each association between a second local identifier of the one or more second local identifiers and the new item code, wherein the data storage object comprises the new item code and the second local identifier; and store each of the generated data storage objects in a different data store.

15. The system of claim 14, wherein the one or more processors are configured to execute instructions to cause the system to:

determine, based at least in part on the second local identifier stored it the generated data storage object, a second client system of the plurality of second client systems; and grant access to the second client system for a data store storing the data storage object that comprises the second local identifier.

16. The system of claim 10, wherein the one or more processors are configured to execute instructions to cause the system to:

receive, from the first client system, drug information related to the new item code, wherein the item code includes a drug code;

determine, based at least in part on the drug information, a platform identifier; and determine, based at least in part on the platform identifier, one or more second local identifiers when the first local identifier does not exist.

17. The system of claim 10, wherein the one or more processors are configured to execute instructions to cause the system to:

determine, based at least in part on the first local identifier, one or more third local identifiers when the first local identifier exists, wherein the one or more third local identifiers are used by the first client system; and provide an instruction to the first client system to associate the one or more third local identifiers with the new item code.

18. The system of claim 10, wherein the one or more processors are configured to execute instructions to cause the system to:

determine the one or more second local identifiers based on a platform identifier associated with first local identifier.

\* \* \* \* \*